(12) United States Patent
Blake, III

(10) Patent No.: US 10,098,641 B1
(45) Date of Patent: Oct. 16, 2018

(54) JAWS AND CAMS FOR CLIP APPLYING INSTRUMENTS

(71) Applicant: Joseph W Blake, III, New Canaan, CT (US)

(72) Inventor: Joseph W Blake, III, New Canaan, CT (US)

( * ) Notice: Subject to any disclaimer, the term of this patent is extended or adjusted under 35 U.S.C. 154(b) by 349 days.

(21) Appl. No.: 14/756,281

(22) Filed: Aug. 20, 2015

Related U.S. Application Data

(63) Continuation-in-part of application No. 14/121,344, filed on Aug. 22, 2014.

(60) Provisional application No. 62/070,350, filed on Aug. 21, 2014.

(51) Int. Cl.
*A61B 17/10* (2006.01)

(52) U.S. Cl.
CPC .................................. *A61B 17/105* (2013.01)

(58) Field of Classification Search
CPC ............ A61B 17/0487; A61B 17/0488; A61B 17/068; A61B 17/0682; A61B 17/122; A61B 17/1227; A61B 17/128; A61B 17/1285; A61B 2017/0409; A61B 2017/2932–2017/2936; A61B 17/10; A61B 2017/0488; A61B 2017/049
See application file for complete search history.

(56) References Cited

U.S. PATENT DOCUMENTS

| | | |
|---|---|---|
| 600,504 A | 10/1898 | Autio |
| 1,498,488 A | 6/1924 | Stallings |
| 2,455,833 A | 12/1948 | Trombetta |
| 2,490,741 A | 12/1949 | Pashby |
| 2,744,251 A | 5/1956 | Vollmer |
| 2,927,171 A | 3/1960 | Rhodes |
| 2,959,172 A | 11/1960 | Held |
| 3,047,874 A | 8/1962 | Kelsey |
| 3,098,232 A | 7/1963 | Brown |
| 3,120,230 A | 2/1964 | Skold |
| 3,230,758 A | 1/1966 | Klingler |
| 3,263,504 A | 8/1966 | Parkinson |
| 3,545,444 A | 12/1970 | Green |
| RE27,146 E | 6/1971 | Rozmus |
| 3,638,847 A | 2/1972 | Noiles et al. |
| 3,646,801 A | 3/1972 | Caroli |
| 3,777,538 A | 12/1973 | Weatherly |
| 3,819,100 A | 6/1974 | Noiles |
| 3,844,289 A | 10/1974 | Noiles |
| 3,949,924 A | 4/1976 | Green |
| 4,166,466 A | 9/1979 | Jarvik |
| 4,196,836 A | 4/1980 | Becht |
| 4,204,623 A | 5/1980 | Green |
| 4,242,902 A | 1/1981 | Green |
| 4,246,903 A | 1/1981 | Larkin |
| 4,296,751 A | 10/1981 | Blake, III et al. |
| 4,367,746 A | 1/1983 | Derechinsky |
| 4,372,316 A | 2/1983 | Blake, III et al. |

(Continued)

*Primary Examiner* — Eric Rosen
*Assistant Examiner* — Mikail Mannan

(57) ABSTRACT

A novel jaw and cam ensemble for use in a medical clip applying instrument having a compressible grip assembly at one end and a pair of squeezable jaws at the opposite end. Included is an elongated operating means connecting the cam and jaw ensemble to the compressible grips for the purpose of translating motion one to the other and for sequential advancement and closure of a plurality of clips between the jaws.

17 Claims, 7 Drawing Sheets

(56) References Cited

U.S. PATENT DOCUMENTS

| | | |
|---|---|---|
| 4,408,603 A | 10/1983 | Blake, III et al. |
| 4,425,915 A | 1/1984 | Ivanov |
| 4,430,997 A | 2/1984 | DiGiovanni et al. |
| 4,448,194 A | 5/1984 | DiGiovanni |
| 4,480,640 A | 11/1984 | Becht |
| 4,492,232 A | 1/1985 | Green |
| 4,532,925 A | 7/1985 | Blake, III |
| 4,562,839 A | 1/1986 | Blake, III |
| 4,572,183 A | 2/1986 | Juska |
| 4,616,650 A | 10/1986 | Green et al. |
| 4,624,254 A | 11/1986 | McGarry et al. |
| 4,662,374 A | 5/1987 | Blake, III |
| 4,850,355 A | 7/1989 | Brooks et al. |
| 5,047,038 A | 9/1991 | Peters et al. |
| 5,084,057 A | 1/1992 | Green et al. |
| 5,100,420 A | 3/1992 | Green et al. |
| 5,104,395 A | 4/1992 | Thornton et al. |
| 5,171,247 A | 12/1992 | Hughett |
| D332,660 S | 1/1993 | Rawson |
| 5,192,288 A | 3/1993 | Thompson et al. |
| 5,271,727 A | 12/1993 | Haber et al. |
| 5,289,963 A | 3/1994 | McGarry et al. |
| 5,290,302 A | 3/1994 | Pericic |
| 5,308,357 A | 5/1994 | Lichtman |
| 5,366,134 A | 11/1994 | Green et al. |
| 5,370,658 A | 12/1994 | Scheller et al. |
| D354,564 S | 1/1995 | Medema |
| 5,403,327 A | 4/1995 | Thornton et al. |
| 5,431,668 A | 7/1995 | Burbank, III et al. |
| 5,484,095 A | 1/1996 | Green et al. |
| 5,527,318 A | 6/1996 | McCarry |
| 5,527,326 A | 6/1996 | Herman et al. |
| 5,591,178 A | 1/1997 | Green et al. |
| 5,607,436 A | 3/1997 | Pratt et al. |
| 5,623,854 A | 4/1997 | Snider |
| 5,634,930 A | 6/1997 | Thornton et al. |
| 5,645,551 A | 7/1997 | Green et al. |
| 5,681,330 A | 10/1997 | Hughett et al. |
| 5,700,270 A | 12/1997 | Peyser et al. |
| 5,700,271 A | 12/1997 | Whitfield et al. |
| 5,720,756 A | 2/1998 | Green et al. |
| 5,725,537 A | 3/1998 | Green et al. |
| 5,725,538 A | 3/1998 | Green et al. |
| 5,833,696 A | 11/1998 | Whitfield et al. |
| 5,833,698 A | 11/1998 | Hinchliffe et al. |
| 5,868,761 A | 2/1999 | Nicholas et al. |
| 5,893,873 A | 4/1999 | Rader et al. |
| 5,904,693 A | 5/1999 | Dicesare et al. |
| 5,938,667 A | 8/1999 | Peyser |
| 5,951,574 A | 9/1999 | Stefanchik et al. |
| 5,993,465 A | 11/1999 | Shipp |
| 6,024,748 A | 2/2000 | Manzo et al. |
| 6,171,316 B1 | 1/2001 | Kovac et al. |
| 6,277,131 B1 | 8/2001 | Kalikow |
| 6,348,054 B1 | 2/2002 | Allen |
| 6,423,079 B1 | 7/2002 | Blake, III |
| 6,849,079 B1 | 2/2005 | Blake, III et al. |
| 6,855,156 B2 | 2/2005 | Etter et al. |
| 6,869,435 B2 | 3/2005 | Blake, III |
| 6,911,033 B2 | 6/2005 | De Guillebon et al. |
| 7,141,056 B2 | 11/2006 | Manetakis |
| 7,261,724 B2 | 8/2007 | Molitor |
| 7,264,625 B1 | 9/2007 | Buncke |
| 7,288,098 B2 | 10/2007 | Huitema |
| 7,297,149 B2 | 11/2007 | Vitali |
| 7,585,304 B2 | 9/2009 | Hughett |
| 7,621,926 B2 | 11/2009 | Wixey et al. |
| 7,637,917 B2 | 12/2009 | Whitfield et al. |
| 7,717,926 B2 | 5/2010 | Whitfield et al. |
| 7,731,724 B2 | 6/2010 | Huitema |
| 8,075,571 B2 | 12/2011 | Vitali |
| 8,172,870 B2 | 5/2012 | Shipp |
| 8,187,287 B1 | 5/2012 | Blake |
| 8,236,012 B2 | 8/2012 | Vitali |
| 8,262,679 B2 | 9/2012 | Nguyen |
| 8,267,944 B2 | 9/2012 | Sorrentino |
| 8,267,945 B2 | 9/2012 | Nguyen |
| 8,267,946 B2 | 9/2012 | Whitfield |
| 8,282,655 B2 | 10/2012 | Whitfield |
| 8,357,171 B2 | 1/2013 | Whitfield |
| 8,409,223 B2 | 4/2013 | Sorrentino |
| 8,480,688 B2 | 7/2013 | Boulnois |
| 8,496,673 B2 | 7/2013 | Nguyen |
| 8,523,882 B2 | 9/2013 | Huitema |
| 8,529,588 B2 | 9/2013 | Ahlberg |
| 8,545,486 B2 | 10/2013 | Malkowski |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,894,665 B2 | 11/2014 | Sorrentino et al. |
| 8,915,930 B2 | 12/2014 | Huitema |
| 8,920,438 B2 | 12/2014 | Aranyi et al. |
| 8,968,337 B2 | 3/2015 | Whitfield et al. |
| 9,011,464 B2 | 4/2015 | Zammataro |
| 9,011,465 B2 | 4/2015 | Whitfield |
| 9,089,334 B2 | 7/2015 | Sorrentino |
| 9,113,892 B2 | 8/2015 | Malkowski |
| 9,113,893 B2 | 8/2015 | Sorrentino |
| 9,186,153 B2 | 11/2015 | Zammataro |
| 9,271,737 B2 | 3/2016 | Castro et al. |
| 9,326,776 B2 | 5/2016 | Gadberry et al. |
| 9,491,608 B2 | 11/2016 | Naito et al. |
| 2002/0002374 A1 | 1/2002 | Barreiro |
| 2002/0049472 A1 | 4/2002 | Coleman |
| 2002/0128668 A1 | 9/2002 | Manetakis et al. |
| 2003/0014060 A1 | 1/2003 | Wilson |
| 2003/0023249 A1 | 1/2003 | Manetakis |
| 2003/0135224 A1 | 7/2003 | Blake, III |
| 2007/0093856 A1* | 4/2007 | Whitfield ............ A61B 17/1285 606/142 |
| 2008/0140090 A1 | 6/2008 | Aranyi |
| 2011/0144665 A1 | 6/2011 | Malkowski |
| 2013/0165951 A1 | 6/2013 | Blake, III |
| 2014/0052157 A1 | 2/2014 | Whitfield |
| 2014/0379003 A1 | 12/2014 | Blake, III |
| 2015/0005790 A1 | 1/2015 | Whitfield et al. |

* cited by examiner

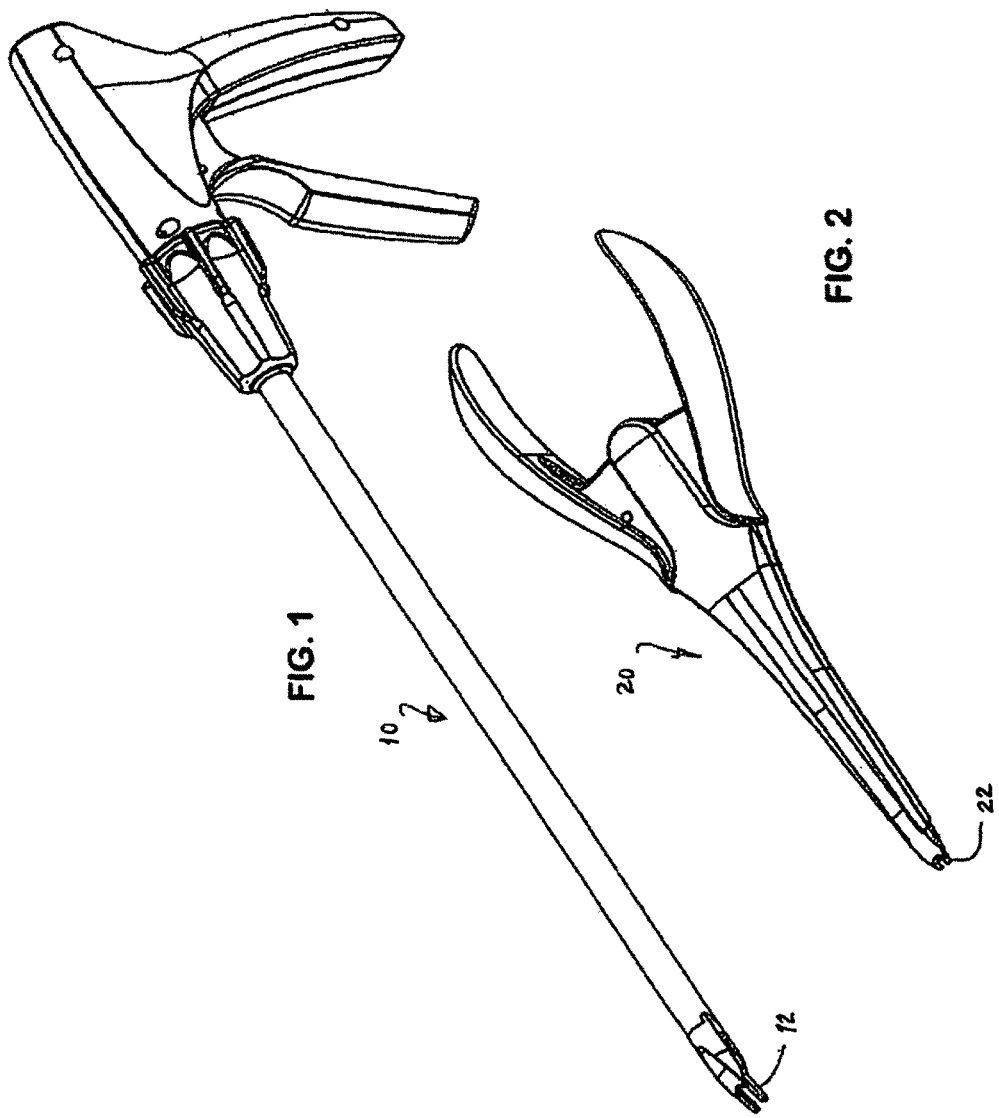

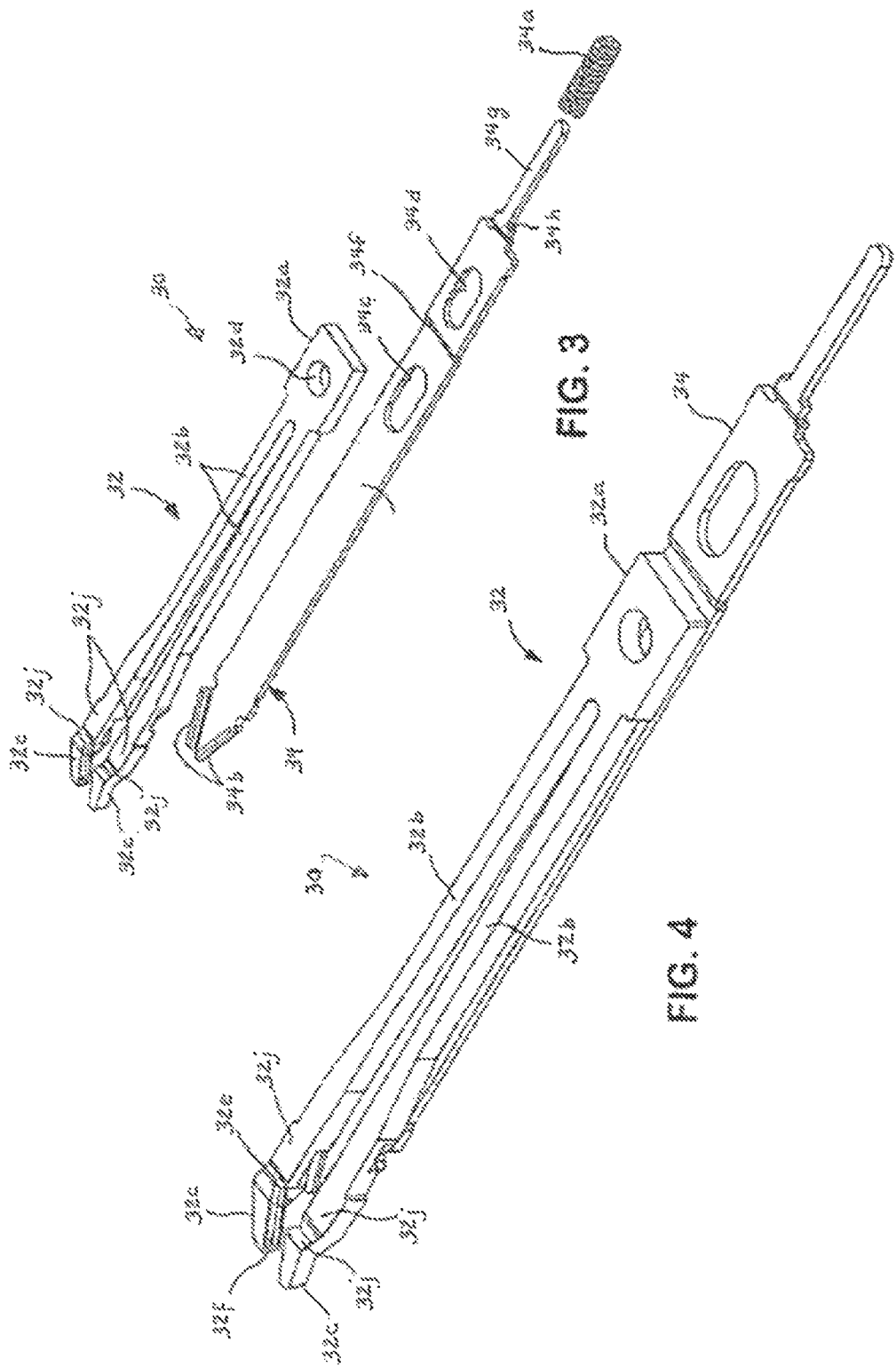

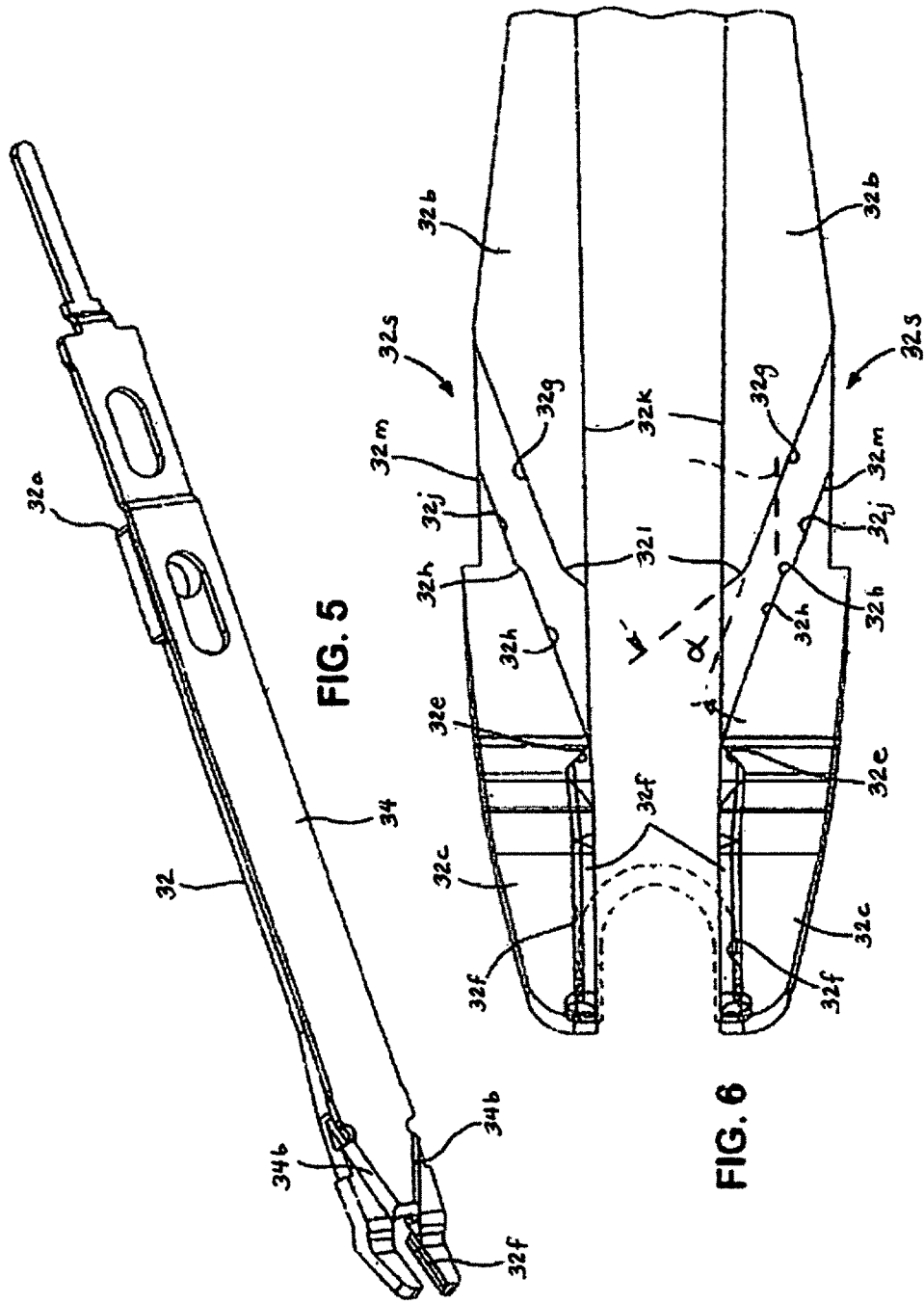

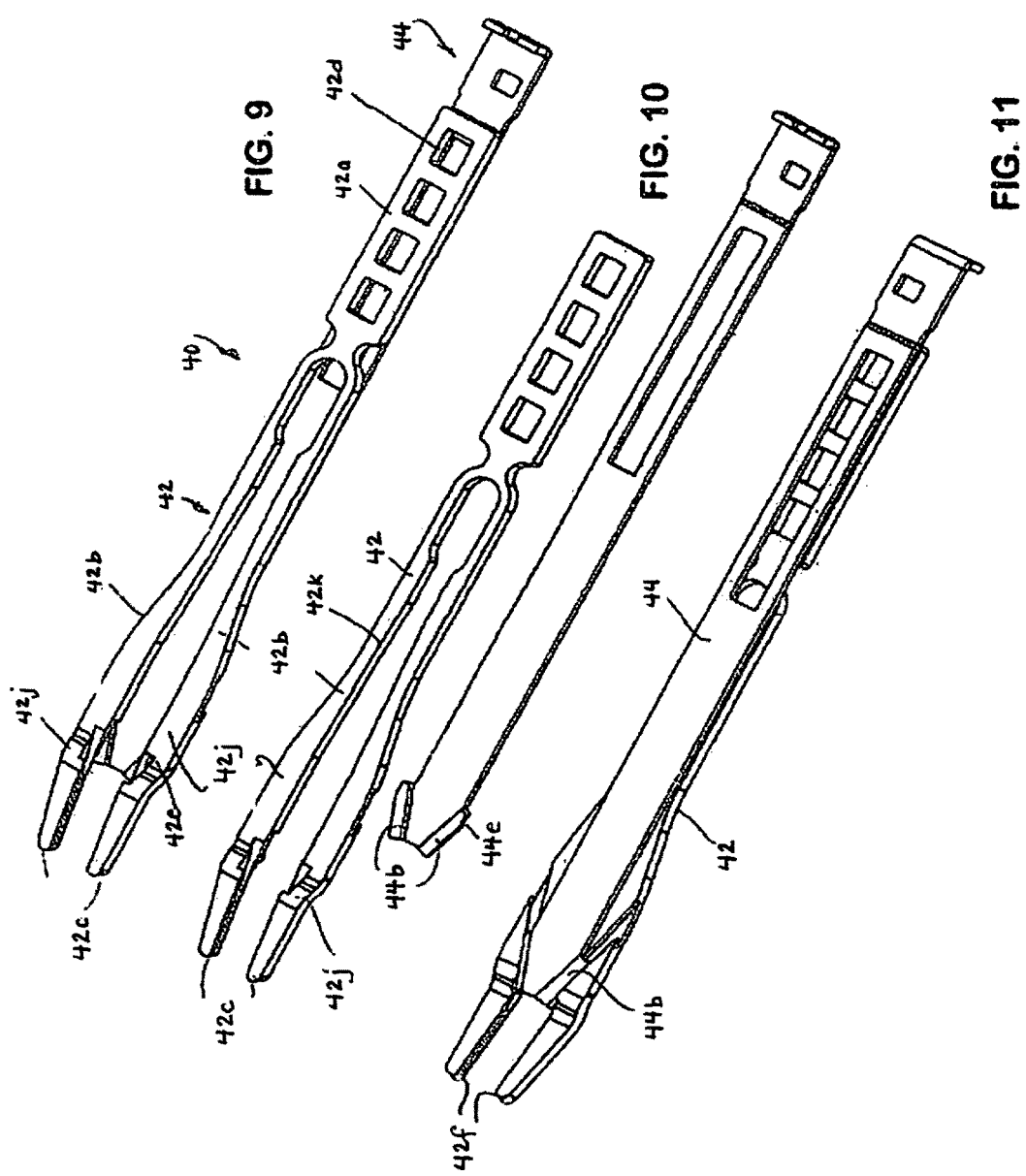

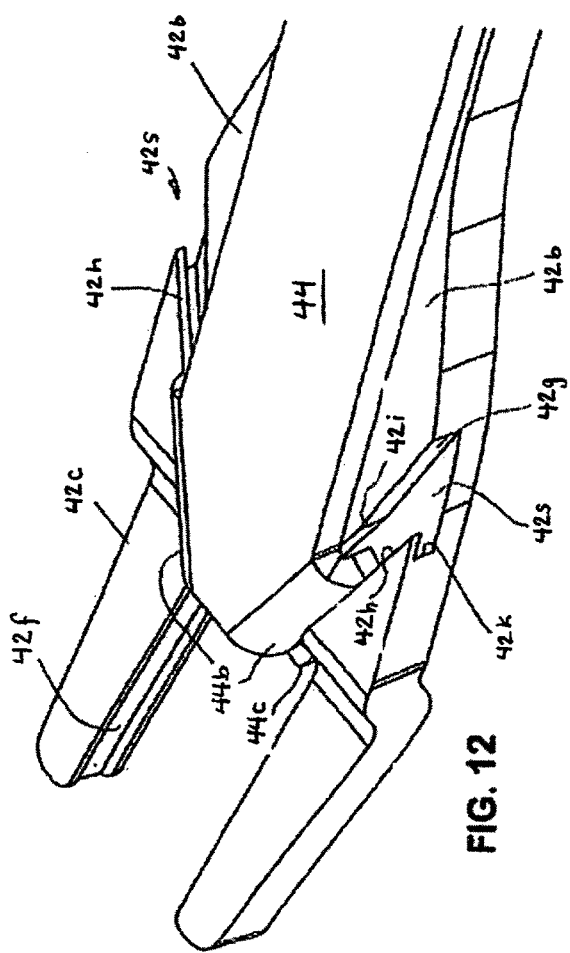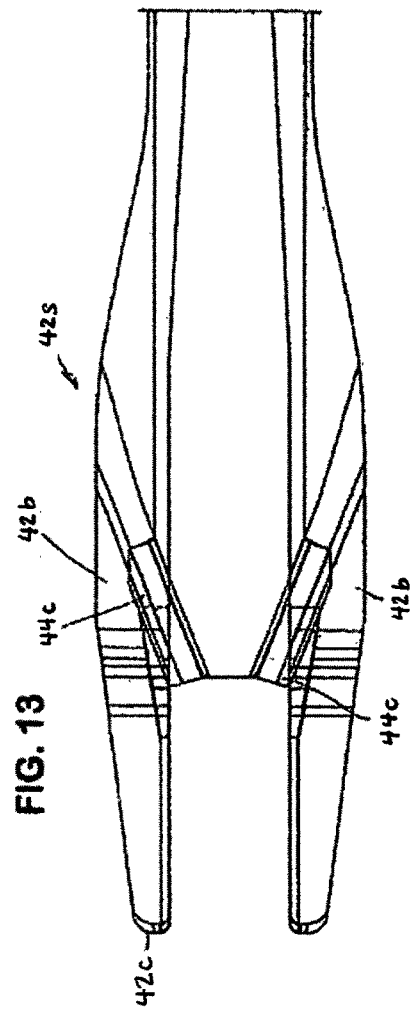

JAWS AND CAMS FOR CLIP APPLYING INSTRUMENTS

PRIORITY

This application claims priority of U.S. Provisional application of Joseph W Blake III Ser. No. 62/070,350 dated Aug. 21, 2014 entitled Jaws and Cams for Clip Applying Instruments the entire content of which is relied upon and fully incorporated herein by reference.

This application is a continuation-in-part of U.S. patent application Ser. No. 14/121,344 filed Aug. 22, 2014 entitled A Instrument for Serially Applying Clips to a Surgical Site the entire contents of which are relied upon and are fully incorporated herein by reference.

FIELD OF THE INVENTION

The present invention relates to clip appliers as instruments for closing vessels in surgical procedures, and more particularly to jaws and cams embodied in such instruments.

BACKGROUND OF THE INVENTION

A preferred embodiment of an instrument according to the present invention is particularly suitable for surgical procedures including laparoscopic and open surgery.

Conventional suturing techniques have given way to the use of surgical clips applied at the junction of vessels or tissue parts to be joined where the clips perform a holding action akin to that of sutures. Hemostatic clips are used for tying off bleeding blood vessels in surgery and in traumatic medical intervention. Here a clip applier with opposed jaws crimps (or flattens) a U-shape clip over a blood vessel to close its lumen. These clips are also used to close other fluid ducts during surgery.

Jaws and cam pusher bars are conventional elements of clip applying medical instruments and typically function as follows: The cam bar pushes distally against outer ramps disposed on both sides of the fixedly mounted jaws urging them to come together and close a malleable hemostatic clip stationed between the jaws thereby ceasing fluid flow through the clip surrounded vein. The jaw is fork shaped having flexible leg portions supporting the distal jaw tips and acting as biasing means for returning the jaw tips to the open position when stroke is complete. Some disadvantages of this arrangement are:
1. A stroke reversing mechanism is needed to coordinate the clip feeding and jaw closing cycle in a single stroke necessitating increased mechanical complexity.
2. Excessive jaw width is needed to compensate for ramp height. This expands the width of the opening the instrument can access.

Though the jaw width issue is not addressed in the following Blake patent references, U.S. Pat. No. 6,423,079; U.S. Pat. No. 6,869,435; and US applications No. 2013/0165951; and Ser. No. 13/987,017, these Blake patents and applications reflect elimination of the disadvantageous stroke reversing mechanism.

SUMMARY OF THE INVENTION

The present invention provides two interactive components for use in serially clip fed surgical clip applying instruments.

The first component is forked shaped jaws without conventional external ramps projecting laterally outward. The jaws have fixed contact points in one face, flexible leg portions for biasing the jaw halves to an open position following closure, and are operable on a pull stroke of the cam.

The second component is a cam pulling bar with angled cam surfaces vertically disposed at its distal end and means for receiving the pulling forces generated by the instrument's compressible grips at the proximal end.

The cam bar when assembled to the jaws rests in a relaxed state with the distal cam surfaces in contact with fixed contact points of the jaw faces. Clip closure is achieved when the cam bar is pulled proximally causing the jaw tips to come together cinching the clip and the encapsulated fluid conducting vessel causing a cessation of fluid flow therein.

In a preferred embodiment of clip applying instrument having jaws and cam bar components described herein and in parent application identified above, clip crimping jaws apply a clip with a rearward movement of a jaw cam member thereby allowing the functions of clip loading and jaw closure to be coordinated and operated by sliding cam bar and actuating bar moving reciprocally to load and fire clips.

The clip actuating mechanism of parent application Ser. No. 14/121,344 includes a actuating bar and in-line clip supply channel working together so that with a squeeze of the operating handle, the actuating bar moves rearward in the instrument closing the jaws to apply a clip in surgery, a clip retractor linked to the actuating bar pulls the stack of clips rearward leaving the foremost clip in the jaws for individual closure around a blood (or other) vessel, and that with release of the operating handles, the jaws open, the next clip is loaded into the jaws, and the instrument is ready to apply another clip.

Specific examples of jaws and cam bar components of this invention are included in the following description for purposes of clarity, but various details can be changed within the scope of the present invention.

OBJECTS OF THE INVENTION

An object of the invention is to provide jaws and cams for a clip applier instrument.

A another object of the invention is to provide an assembly of cooperating jaws and cam bar for receiving reciprocating motion from instrument components so as to close and open the jaws for applying clips at a surgical site.

A another object of the invention is to provide an assembly of cooperating jaws and cam bar having an operating mechanical advantage that does not diminish as cam bar closes the jaws.

A another object of the invention is to provide an assembly of cooperating jaws and cam bar having cam grooves that prevent a binding condition when jaw arms move to closed position.

A further object of the invention is to provide an assembly of cooperating jaws and cam bar held in engagement with jaw heads in parallel configuration.

Other and further objects of the invention will become apparent with an understanding of the following detailed description of the invention or upon employment of the invention.

BRIEF DESCRIPTION OF THE DRAWING

Preferred embodiment of the invention have been chosen for detailed description to enable those having ordinary skill in the art to which the invention appertains to readily understand how to construct and use the invention and is shown in the accompanying drawing in which:

FIG. 1 is a perspective view of typical laparoscopic clip applying instrument in which the jaws and cam of the present invention may be incorporated.

FIG. 2 is a perspective view of open surgical clip applying instrument in which the jaws and cam of the present invention may be incorporated.

FIG. 3 is an exploded top perspective view of jaw and cam for clip applying instruments according to the invention.

FIG. 4 is a top perspective view of an assembly of jaw and cam illustrated in FIG. 3.

FIG. 5 is a bottom perspective view of an assembly of jaws and cam illustrated in FIG. 4.

FIG. 6 is a bottom plan view of jaws of FIG. 3 showing cam grooves.

FIG. 9 is a top perspective view of a modified embodiment of an assembly of jaws and cam.

FIG. 10 is an exploded top perspective view of jaws and cam of FIG. 9.

FIG. 11 is a bottom perspective view of an assembly of jaws and cam of FIG. 9.

FIG. 12 is an enlarged bottom perspective view of assembly of jaws and cam of FIG. 9.

FIG. 13 is an bottom plan view of an assembly of jaws and cam of FIG. 9.

DETAILED DESCRIPTION OF THE PREFERRED EMBODIMENT

Figure 7:
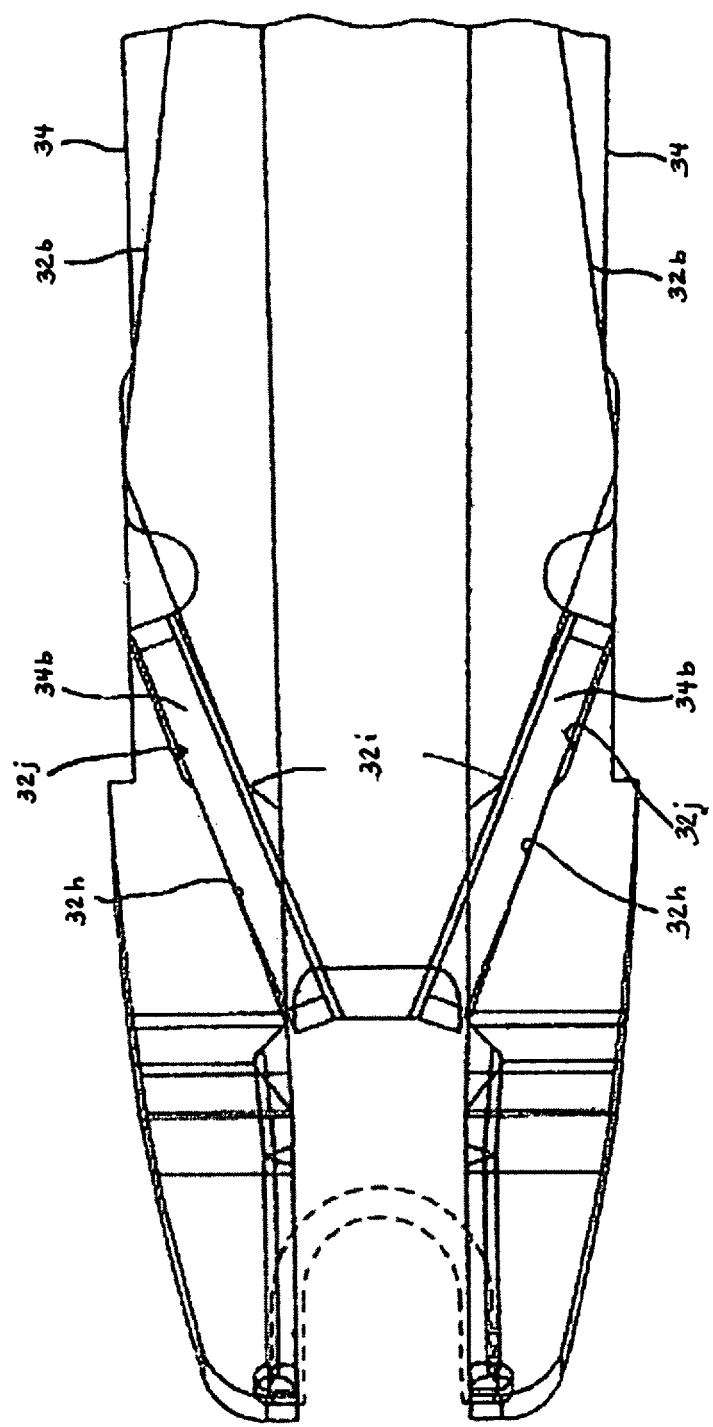
FIG. 7 is bottom plan view of assembled jaws and cam bar of FIG. 4.
Figure 8:
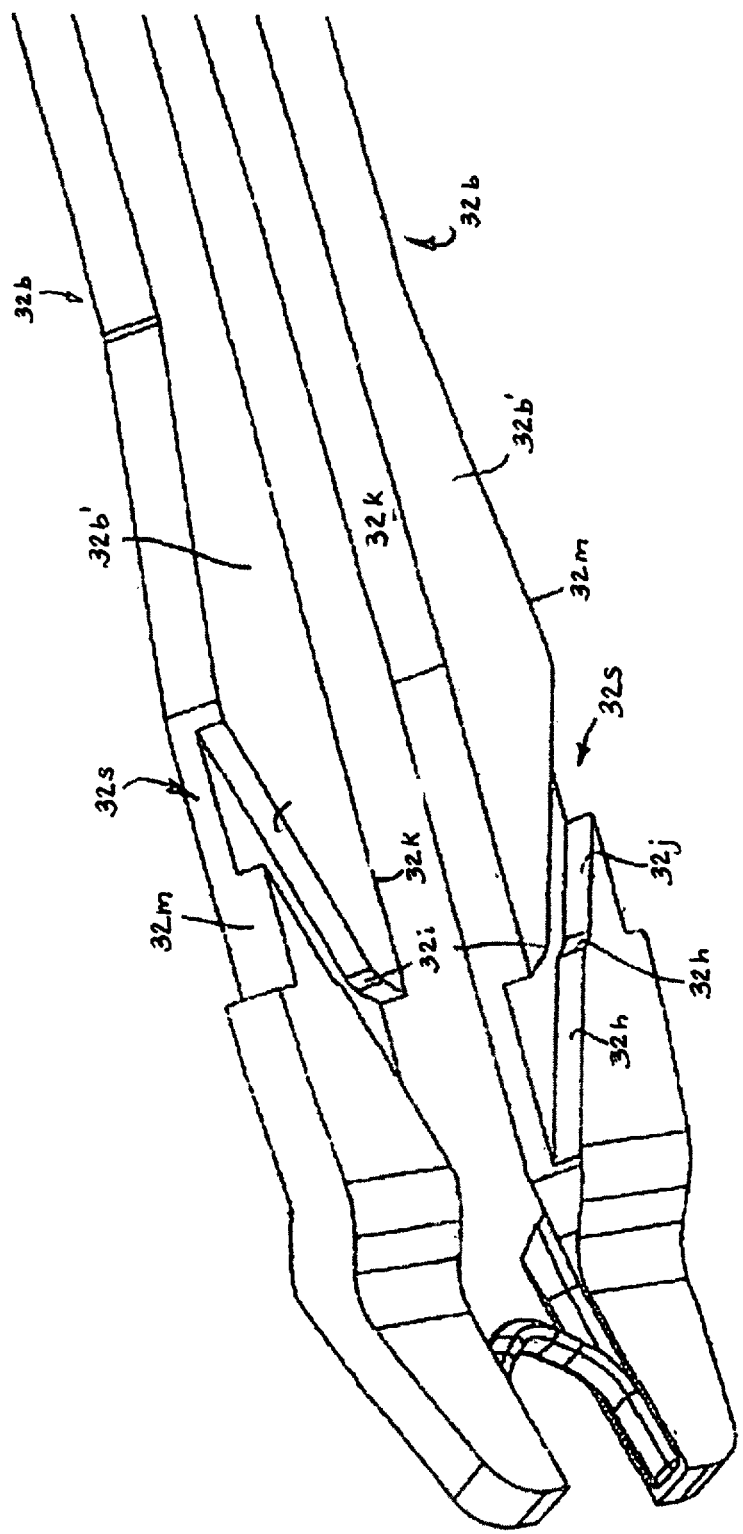
FIG. 8 is bottom perspective view of jaws showing cam bar contact points, relief notches, and typical clip in place.

FIG. 1 shows a typical laparoscopic clip applying instrument 10 with clip applying jaws 12 located at distal end.

FIG. 2 shows an open surgery clip applying instrument 20 with clip applying jaws 22 located at distal end.

FIGS. 3-8 show jaws and cam bar assembly 30 according to the invention. Jaws 32 overlie cam bar 34 that receives linear reciprocating motion from puller bar (not shown) of clip applying instrument wherein cam bar moving proximally cams jaws closed as part of operating sequence of instrument components. When cam bar moves distally, jaws spring open.

Jaws 32 comprise base plate 32a with jaw spring arms 32b extending in parallel from the base terminating in cooperating jaw heads 32c. The base plate has aperture 32d for securing the jaws to jaw post (not shown) of the instrument chassis.

Jaw heads 32c have jaw steps 32j locating jaws above arm surface 32j' with jaws canted downwardly for establishing entry points 32e where clips move into jaws. The jaw heads have confronting inner surface clip grooves 32f for receiving open clips delivered by clip handling mechanisms. The jaw arms have a natural spring bias to jaw-open position and are forced closed by cam bar ramps 34b engaging cam grooves for crimping a clip in surgery.

The under faces 32b' (FIG. 6-8) of each spring arm have cam grooves 32s extending diagonally across spring arms converging toward jaw heads. Cam grooves are defined by spaced proximal 32g and distal 32h cam walls extending diagonally across jaw arms. Each proximal wall turns toward arm inner surface 32k to define a crowned point or edge 32i that contacts the cam bar ramps 34b. Crowned (or contact) point 32i concentrates force from cam bar ramp 34b at a fixed location such that the mechanical advantage between cam and ramp does not negatively shift as cam bar 34 moves proximally to close the jaws. As shown in FIG. 6, each proximal wall turns toward inner surface 32k thus forming an angle $\alpha$ with wall extension 32g'. Angle $\alpha$ has a range of 20° to 60° and preferably is approximately 40°. Crown point is located preferably between jaw arm midline ML and inner wall 32k.

Distal walls 32h are provided with relief notches 32j between distal wall midpoint 32h' to jaw arm outer surface 32m. As best shown in FIG. 7, relief notches 32j provide a separation space between surface of distal wall 32h and near distal surface of cam ramp 34b so as to prevent a binding condition between ramp and groove when jaw arms flex to closed position of jaws.

FIGS. 9-13 show another preferred embodiment 40 of assembly of jaws 42 and cam bar 44 according to the invention. Jaws 42 overlie cam bar 44 that receives linear reciprocating motion from puller bar (not shown) of clip applying instrument wherein cam bar moving proximally cams close jaws as part of operating sequence of instrument components. When cam bar moves distally, jaws spring open.

Jaws 42 comprise base plate 42a with jaw spring arms 42b extending in parallel from the base terminating in cooperating jaw heads 42c. Jaw arms constitute spring beams maintaining outward force to open jaws and receive a fresh clip following a cam induced closure. In operation, jaw arms are wedged apart by action of cam ramps 44b in jaw arm grooves 42s. The base plate has apertures 42d for securing the jaws to fixed post (not shown) of the instrument chassis.

Jaw heads 42c have jaw steps 42j locating jaws above arm surface 42j' with jaws canted downwardly for establishing entry points 42e where clips move into jaws. The jaw heads have confronting inner surface clip grooves 42f for receiving open clips delivered by clip handling mechanisms. The jaw arms have a natural spring bias to jaw-open position and are forced closed by cam-bar ramps 44b engaging cam grooves for crimping a clip in surgery.

The under faces 42b (FIGS. 11-13) of each spring arm have cam grooves 42s extending diagonally across spring arms converging toward jaw heads. Cam grooves are defined by spaced proximal 42g and distal 42h cam walls extending diagonally across jaw arms. Each proximal wall turns toward arm inner surface 42k to define a crowned point or edge 42i that contacts the cam bar ramps 44b. Crowned (or contact) point 42i concentrates force from cam bar ramp 44b at a fixed location such that the mechanical advantage between cam and ramp does not negatively shift as cam bar 44 moves proximally to close the jaws. The location and geometry of crown point 42i is the same as recited above for the embodiment of FIGS. 1-8.

Distal walls 42h are provided with undercuts 42k extending the full length of each cam groove 42s. The groove wall undercuts receive cam ramp fold over lips 44c to lock ramp and groove together so as to prevent jaw head misalignment.

The jaws and cam arrangement of the invention has an operating mechanical advantage that does not diminish as cam bar closes the jaws, cam groove relief notches that prevent a binding condition when jaw arms move to closed position, and are held in engagement with jaw heads in parallel configuration.

The cam puller of this patent application is, by virtue of its ramp angles, the prime determinant of the force/stroke vector that will result in a satisfactory clip closure as regards clip sizes and wire characteristics.

The jaws are the recipient of the sliding contact pressure of the cam ramps as concentrated at single fixed points located on the proximal vertical walls of the jaw grooves.

The jaw groove profile conforms generally to that of the cam puller ramp with additional relief provided to compensate for angular jaw deflection during closure. On the pulling stroke, the cam ramps are in contact only with the designated fixed points of the jaw grooves.

On the return stroke, the opposing jaw groove walls interact with the opposite sides of the cam ramps to wedge the jaws back to the open position.

The term approximately for purposes of this application means plus or minus 10% of the values stated.

Various changes may be made to the structure embodying the principles of the invention. The foregoing embodiments are set forth in an illustrative and not in a limiting sense. The scope of the invention is defined by the claims appended hereto.

I claim:

1. An assembly for an instrument for applying clips in surgery, the assembly comprising
    jaws having a base and jaw arms, each jaw arm extending from the base to a distal jaw point; and
    a cam bar with ramps;
    each jaw arm having a top surface, an under surface, an inner surface and an outer surface, the under surface of each of the jaw arms having a cam groove extending from the outer surface to the inner surface,
    the cam grooves having spaced and angled proximal and distal cam walls, the cam grooves extending between the proximal and distal cam walls, the cam grooves extending distally inward in a diagonal direction towards a longitudinal axis of the assembly such that a proximal end of the cam grooves is further from the longitudinal axis than a distal end of the cam grooves, the distal cam walls terminating distally of the proximal cam walls,
    each proximal cam wall extending distally at an angle and extends further to an angle more inwardly angled toward the longitudinal axis to define a crowned point in each proximal cam wall for engaging the ramps of the cam bar,
    the ramps of the cam bar cooperating with the cam grooves for actuating the jaws by pulling the jaws closed and pushing the jaws open, each ramp of the cam bar being in contact with a respective one of the crowned points when the cam bar retracts to close the jaws to maintain mechanical advantage between the jaws and the cam bar as the cam bar closes the jaws, the cam bar movable distally to open the jaws.

2. The assembly as defined in claim 1 in which the crowned point of each jaw arm is located between the inner surface and a median line of the under surface of the respective jaw arm.

3. The assembly as defined in claim 1 in which the proximal cam wall of each jaw arm turns toward the longitudinal axis to form an acute angle with the inner surface of the respective jaw arm and forms an angle alpha to define the crowned point of the respective jaw arm.

4. The assembly as defined in claim 3 in which angle alpha has a range of 20 degrees to 60 degrees.

5. The assembly as defined in claim 3 in which angle alpha is 40 degrees.

6. The assembly of claim 1, wherein, for each jaw arm the distal cam wall has a relief notch facing the cam groove to provide a separation space between a surface of the distal cam wall and a respective one of the ramps of the cam bar.

7. The assembly of claim 1, wherein the jaws have steps canted downwardly to establish entry points for clips.

8. The assembly of claim 1, wherein each cam groove is wider at a distal end than a proximal end.

9. An assembly for an instrument for applying clips in surgery, the assembly comprising:
    jaw having a base and jaw arms, each jaw arm extending in parallel to each other from the base to a distal jaw point; and
    a cam bar having ramps;
    each jaw arm having a top surface, an under surface, an inner surface and an outer surface, the under surface of each of the jaw arms having a cam groove extending diagonally inwardly in a distal direction from the outer surface to the inner surface, the cam grooves having spaced and angled proximal and distal cam walls across the under surfaces of the jaw arms, the cam grooves extending between proximal and distal cam walls; wherein for each jaw arm, the proximal wall turns toward the inner surface to define a crowned point for engaging the ramps of the cam bar; the ramps of the cam bar cooperating with the cam grooves of the law arms for actuating the jaws by pulling the jaws closed and pushing the jaws open, each ramp of the cam bar being in contact with a respective one of the crowned points when the cam bar retracts to close the jaws so as to maintain mechanical advantage that does not diminish as the cam bar closes the jaws, the cam bar movable distally to open the jaws and, for each of the jaw arms the distal cam wall has a relief notch facing the cam groove and spaced distally of a proximal edge of the distal cam walls to prevent a binding condition when the jaw arms flex to a closed position of the jaws.

10. The assembly of claim 9, wherein, for each jaw arm, the relief notch is proximal of the crowned point.

11. The assembly of claim 9, wherein the relief notch of each jaw arm increases a distance between the distal and proximal cam walls.

12. The assembly of claim 9, wherein for each jaw arm an undercut is formed between the cam groove and an outer surface of the distal cam wall so as to be positioned laterally outwardly of the cam groove.

13. The assembly of claim 12, wherein each ramp of the cam bar has a laterally extending fold over lip to prevent misalignment of the jaws.

14. The assembly of claim 12, wherein each lip extends from a lower surface of a respective one of the ramps of the cam bar.

15. An assembly for an instrument for applying clips in surgery, the assembly comprising:
    jaws having a base and jaw arms, each jaw arm extending in parallel to each other from the base to a distal jaw point;
    and a cam bar having ramps;
    each jaw arm having a top surface, an under surface, an inner surface and an outer surface; wherein for each jaw arm, the under surface of the jaw arm has a cam groove extending diagonally inwardly in a distal direction from the outer surface to the inner surface; the cam grooves having spaced proximal and distal cam walls across the under surfaces of the jaw arms; wherein for each jaw arm, the proximal wall turns toward the inner surface to define a crowned point for engaging ramps of the cam bar; the ramps of the cam bar cooperating with the cam grooves for actuating the jaws by pulling the jaws closed and pushing the jaws open, each of the ramps of the cam bar being in contact with a respective one of the crowned points when the cam bar retracts to close the laws so as to maintain mechanical advantage that does not diminish as the cam bar closes the jaws, the cam bar movable distally to open the jaws; wherein for each jaw arm, the distal wall being undercut between the inner and outer surfaces; wherein for each law arm, the undercut is formed between the cam groove and an outer surface of the distal cam wall to be positioned laterally outwardly of the cam groove and each ramp of the cam bar having a fold over lip to lock each ramp of the cam bar and the respective cam groove together so as to prevent misalignment of the jaws.

16. The assembly of claim 15, wherein each fold over lip extends laterally from the cam bar.

17. The assembly of claim 16, wherein each lip travels within one of the undercuts as the cam bar is moved proximally to close the jaws.

* * * * *